(12) United States Patent
Paquet et al.

(10) Patent No.: US 11,213,059 B2
(45) Date of Patent: Jan. 4, 2022

(54) NUTRITIONAL FORMULATIONS AND KITS FOR BARIATRIC INDIVIDUALS

(71) Applicant: MANTRA PHARMA, Brossard (CA)

(72) Inventors: Olivier Paquet, Montreal (CA); Maxime Deslauriers, Blainville (CA)

(73) Assignee: MANTRA PHARMA, Brossard (CA)

( * ) Notice: Subject to any disclaimer, the term of this patent is extended or adjusted under 35 U.S.C. 154(b) by 300 days.

(21) Appl. No.: 16/219,510

(22) Filed: Dec. 13, 2018

(65) Prior Publication Data

US 2019/0191754 A1    Jun. 27, 2019

Related U.S. Application Data

(60) Provisional application No. 62/609,709, filed on Dec. 22, 2017.

(51) Int. Cl.

| | |
|---|---|
| *A23L 33/155* | (2016.01) |
| *A23L 33/16* | (2016.01) |
| *A23L 33/00* | (2016.01) |
| *A61P 3/02* | (2006.01) |
| *A61K 33/06* | (2006.01) |
| *A23L 33/15* | (2016.01) |
| *A61K 45/06* | (2006.01) |

(52) U.S. Cl.
CPC ............ *A23L 33/155* (2016.08); *A23L 33/15* (2016.08); *A23L 33/16* (2016.08); *A23L 33/30* (2016.08); *A61K 33/06* (2013.01); *A61K 45/06* (2013.01); *A61P 3/02* (2018.01); *A23V 2002/00* (2013.01); *A23V 2200/30* (2013.01); *A23V 2200/332* (2013.01); *A23V 2250/1578* (2013.01); *A23V 2250/1586* (2013.01); *A23V 2250/1588* (2013.01); *A23V 2250/1592* (2013.01); *A23V 2250/1598* (2013.01); *A23V 2250/16* (2013.01); *A23V 2250/161* (2013.01); *A23V 2250/1604* (2013.01); *A23V 2250/1608* (2013.01); *A23V 2250/1612* (2013.01); *A23V 2250/1614* (2013.01); *A23V 2250/1626* (2013.01); *A23V 2250/1642* (2013.01); *A23V 2250/702* (2013.01); *A23V 2250/705* (2013.01); *A23V 2250/706* (2013.01); *A23V 2250/708* (2013.01); *A23V 2250/7042* (2013.01); *A23V 2250/7044* (2013.01); *A23V 2250/7046* (2013.01); *A23V 2250/7052* (2013.01); *A23V 2250/7054* (2013.01); *A23V 2250/7056* (2013.01); *A23V 2250/7058* (2013.01); *A23V 2250/71* (2013.01); *A23V 2250/7102* (2013.01); *A23V 2250/712* (2013.01); *A23V 2250/7104* (2013.01); *A23V 2250/714* (2013.01); *A23V 2250/7106* (2013.01); *A23V 2250/72* (2013.01)

(58) Field of Classification Search
CPC ........ A23L 33/155; A23L 33/30; A23L 33/16; A23L 33/15; A61P 3/02; A61K 33/06; A61K 45/06
See application file for complete search history.

(56) References Cited

U.S. PATENT DOCUMENTS

| | | | | |
|---|---|---|---|---|
| 8,372,442 B2 * | 2/2013 | Sliwinski | ............... | A61P 19/08 424/646 |
| 8,491,889 B1 * | 7/2013 | Galton | .................... | A23L 33/15 424/94.1 |
| 2011/0081400 A1 * | 4/2011 | Langford | ............... | A23L 33/15 424/439 |
| 2017/0290364 A1 * | 10/2017 | Hamer | .................. | A61K 33/06 |

OTHER PUBLICATIONS

Vitamins and Minerals. 2020. https://www.webmd.com/vitamins-and-supplements/vitamins-minerals-how-much-should-you-take#2.*
Mechanick et al. Clinical Practice Guidlinjes for the Perioperative Nutritional, Metabolic, and Nonsurgical Support of the Bariatric Surgery Patient. Obesity (Silver Spring). 2013.*
Thiamin. 2020. https://ods.od.nih.gov/factsheets/Thiamin-HealthProfessional/.*
St. Joseph's . . . Vitamin and Mineral Supplements in the Bariatric Program. 2013. https://www.stjoes.ca/patients-visitors/patient-education/a-e/PD%208257%20Liquid%20and%20chewable%20vitamins%20for%20Bariatric%20Program.pdf.*
Supplementation After Bariatric Surgery. 2017. https://www.obesityaction.org/wp-content/uploads/Supplementation-after-Bariatric-Surgery.pdf.*
Dimitrios et al. After Bariatric Surgery . . . 2009. Clinical Endocrinology. vol. 71. pp. 322-325.*
Calcium. New World Encyclopedia. 2015. https://www.newworldencyclopedia.org/entry/Calcium.*
Dagan et al. Nutritional Recommendations for Adult Bariatric Surgery Patients. Mar. 2017. https://www.ncbi.nlm.nih.gov/pmc/articles/PMC5347111/.*

\* cited by examiner

*Primary Examiner* — Anthony J Weier
(74) *Attorney, Agent, or Firm* — BCF LLP

(57) ABSTRACT

The present technology relates to a nutritional formulation for administration to bariatric individuals. The nutritional formulation includes a multi-nutrients dosage unit; and a minerals dosage unit.

14 Claims, No Drawings

NUTRITIONAL FORMULATIONS AND KITS FOR BARIATRIC INDIVIDUALS

CROSS-REFERENCE TO RELATED APPLICATION

This application claims the benefit of and priority to U.S. provisional patent application No. 62/609,709, filed on Dec. 22, 2017; the content of which is herein incorporated in entirety by reference.

FIELD OF TECHNOLOGY

The present disclosure generally relates to nutritional formulations, nutritional methods as well as to nutritional kits that strengthens and promotes the general health of bariatric individuals.

BACKGROUND INFORMATION

Bariatric surgical procedures represent a successful way to achieve significant weight reduction in morbidly obese individuals.

Bariatric surgical procedures generally include restrictive procedures and a combination of restrictive/malabsorptive procedures. Restrictive procedures reduce the size of the stomach by banding, stapling, filling space in the stomach with an inflatable balloon or the like, but attempt to leave the digestive process largely intact. Restrictive/malabsorptive combination procedures reduce both the size of the stomach and the amount of nutrients and calories absorbed by the digestive system.

Due to the stresses and changes to the digestive system caused by the various obesity surgery procedures, patients who undergo such procedures often suffer from one or more immediate post-operative complications, such as malnutrition, nutrients deficiencies, dumping syndrome, dehydration, constipation, vomiting, nausea, and weight gain. Nausea and vomiting are the most common complications occurring within the first few months after bariatric surgery. These symptoms may occur after eating too fast, drinking liquids while eating, not chewing enough, or eating more than the gastric pouch of significantly smaller post-surgical size can comfortably hold. Dehydration is also an important concern in post-bariatric surgery patients. Dehydration can be prevented by drinking water or low-calorie beverages between meals (when there is no food in the stomach). Dumping syndrome is another common post-surgical complication and occurs when food passes too quickly from the stomach into the small intestine. Symptoms may include a combination of nausea, uncomfortable fullness, cramping, and diarrhea, or weakness, sweating, and fast heart rate.

Since the size of the stomach is reduced after bariatric surgery and can only hold approximately small amounts at a time, it is often quite challenging for post-operative patients to consume adequate amounts of food and liquid to maintain even minimally acceptable levels of nutrition and hydration. As such, many post-bariatric surgery patients are faced with challenges of consuming sufficient and/or balanced nutrition.

With the goal to achieve a sufficient and/or balanced nutrition, post-bariatric surgery patients are often prescribed with off-the-counter supplements (e.g., Centrum® Multivitamins). Such supplements are designed for general usages and do not address the specific needs of bariatric individuals. Because these supplements are incomplete for bariatric individuals, they are often accompanied by a prescription for additional supplements (e.g., mineral, vitamins, or the like), thereby multiplying the number of pills/tablets the bariatric individuals has to ingest/swallow.

Therefore, a need exists for nutritional formulations that address the requirements of bariatric individuals and that minimize the number of intakes by the patient.

SUMMARY OF DISCLOSURE

Other aspects and features of the present disclosure will become apparent to those ordinarily skilled in the art upon review of the following description of specific embodiments in conjunction with the accompanying drawings.

According to various aspects, the present technology relates to a nutritional formulation for administration to bariatric individuals; comprising: a multi-nutrients dosage unit; and a minerals dosage unit.

According to various aspects, the present technology relates to the use of the nutritional formulation as defined herein for prevention of nutritional deficiencies in a post-bariatric surgery patient.

According to various aspects, the present technology relates to the use of the nutritional formulation as defined herein for the preparation of a medical nutrition for prevention of nutritional deficiencies in a post-bariatric surgery patient.

According to various aspects, the present technology relates to a nutritional kit comprising: a first type of dosage units comprising a multi-nutrients dosage unit; and a second type of dosage units comprising a minerals dosage unit.

According to various aspects, the present technology relates to a nutritional kit comprising: from about 7 days to about a month-supply of dosage units of a first type, each dosage unit of the first type comprising the multi-nutrients dosage unit; and from about 7 days to about a month-supply of dosage units of a second type, each dosage unit of the second type comprising the minerals dosage unit.

According to various aspects, the multi-nutrients dosage unit of the present technology comprises vitamin $B_3$ in an amount of between about 1 mg and about 100 mg, or between about 10 mg and about 25 mg; or comprises vitamin $B_5$ in an amount of between about 0.4 mg and about 100 mg, or between about 1 mg and about 10 mg, or comprises vitamin $B_6$ in an amount of between about 0.1 mg and about 100 mg, or between about 1 mg and about 2 mg, or comprises vitamin $B_7$ in an amount of between about 1.5 μg and about 100 μg, or between about 25 μg and about 50 μg, or comprises vitamin $B_9$ in an amount of between about 30 μg and about 1000 μg, or between about 200 μg and about 500 μg, or comprises vitamin $B_{12}$ in an amount of between about 0.1 μg and about 2500 μg, or between about 10 μg and about 500 μg, or between about 200 μg and about 500 μg, or comprises vitamin C in an amount of between about 5 mg and about 2000 mg, or between about 50 mg and about 100 mg, or comprises vitamin D in an amount of between about 10 μg and about 100 μg or is between about 400 IU and about 4000 IU; or between about 20 μg and about 100 μg, or between about 25 μg and 50 μg, or comprises any mixtures thereof.

According to various aspects, the multi-nutrients dosage unit of the present technology comprises vitamin $D_3$ in an amount of between about 1 μg and about 65 μg or is between about 40 IU and about 2500 IU, or between about 20 μg and about 100 μs, or between about 25 μg and 50 μs.

According to various aspects, the multi-nutrients dosage unit of the present technology comprises vitamin E in an amount of between about 1 mg and about 1000 mg or is between about 1 IU and about 1500 IU, or between about 10 mg and about 100 mg.

According to various aspects, the multi-nutrients dosage unit of the present technology comprises vitamin K in an amount of between about 6 µm and about 200 µm, or between about 50 µm and about 250 µm.

According to various aspects, the multi-nutrients dosage unit of the present technology comprises between about 1 mg and about 5 g of minerals, between about 1 mg and about 5 g, between about 10 mg and about 5 g, between about 1 mg and about 2 g, between about 10 mg and about 2 g, or between about 10 mg and about 1 g.

According to various aspects, the multi-nutrients dosage unit of the present technology comprises copper in the amount of between about 0.05 mg to about 10 mg, or between about 0.5 mg and about 5 mg.

According to various aspects, the multi-nutrients dosage unit of the present technology comprises chromium in an amount of between about 2 µm and about 500 µm, or between about 10 µm and about 50 µm.

According to various aspects, the multi-nutrients dosage unit of the present technology comprises iodine in an amount of between about 0.01 mg to about 1 mg, or between about 0.1 mg and about 0.25 mg.

According to various aspects, the multi-nutrients dosage unit of the present technology comprises iron in an amount of between about 1 mg and about 150 mg, or between about 10 mg and about 100 mg.

According to various aspects, the multi-nutrients dosage unit of the present technology comprises magnesium in an amount of between about 20 mg and about 500 mg, or between about 25 mg and 100 mg.

According to various aspects, the multi-nutrients dosage unit of the present technology comprises potassium in an amount of between about 0 mg and about 200 mg, or between about 20 mg and about 50 mg.

According to various aspects, the multi-nutrients dosage unit of the present technology comprises selenium in an amount of between about 3.0 µm to about 200 µm, or between about 25 µm and 100 µm.

According to various aspects, the multi-nutrients dosage unit of the present technology comprises manganese in the dosage is between about 0.1 mg and about 10 mg, or between about 1 mg and about 5 mg.

According to various aspects, the multi-nutrients dosage unit of the present technology comprises molybdenum in the dosage is between about 2 µm and about 2000 µm, or between about 10 µm and about 100 µm.

According to various aspects, the multi-nutrients dosage unit of the present technology comprises zinc in the dosage is between 0.5 mg and about 50 mg, or between about 5 mg and about 25 mg.

According to various aspects, the multi-nutrients dosage unit of the present technology comprises between about 50 mg and about 2000 mg of alkaline mineral, or between about 100 mg and about 1000 mg of alkaline mineral.

According to various aspects, the present technology relates to a method for reducing nutritional deficiencies in a post-bariatric surgery patent, the method comprising administering to the patient the nutritional formulation as defined herein.

DETAILED DISCLOSURE

The present technology is explained in greater detail below. This description is not intended to be a detailed catalog of all the different ways in which the technology may be implemented, or all the features that may be added to the instant technology. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which variations and additions do not depart from the present technology. Hence, the following description is intended to illustrate some particular embodiments of the technology, and not to exhaustively specify all permutations, combinations and variations thereof.

As used herein, the singular form "a," "an" and "the" include plural referents unless the context clearly dictates otherwise.

The recitation herein of numerical ranges by endpoints is intended to include all numbers subsumed within that range (e.g., a recitation of 1 to 5 includes 1, 1.5, 2, 2.75, 3, 3.80, 4, 4.32, and 5).

The term "about" is used herein explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. For example, the term "about" in the context of a given value or range refers to a value or range that is within 20%, preferably within 15%, more preferably within 10%, more preferably within 9%, more preferably within 8%, more preferably within 7%, more preferably within 6%, and more preferably within 5% of the given value or range.

The expression "and/or" where used herein is to be taken as specific disclosure of each of the two specified features or components with or without the other. For example, "A and/or B" is to be taken as specific disclosure of each of (i) A, (ii) B and (iii) A and B, just as if each is set out individually herein.

The terms "comprise" and "comprising" are used in the inclusive, open sense, meaning that additional elements may be included. The term "including" is used to mean "including but not limited to." "Including" and "including but not limited to" are used interchangeably.

The terms "co-administration" and "co-administering" refer to both concurrent administration (administration of two or more agents at the same time) and time varied administration (administration of one or more agents at a time different from that of the administration of an additional agent or agents), as long as the agents are present in the patient to some extent at the same time.

As used herein, the term "derivative" refers to a compound that is derived from a similar compound by a chemical reaction.

The term "nutrients" refers to nutrient is a component in foods that an organism uses to survive and grow. As used herein, the term "nutrients" includes macronutrients and micronutrients. Macronutrients provide the bulk energy an organism's metabolic system needs to function while micronutrients provide the necessary cofactors for metabolism to be carried out. Both types of nutrients can be acquired from the environment.

The term "solvate" refers to a pharmaceutically acceptable form of a specified compound, with one or more solvent molecules, that retains the biological effectiveness of such compound. Examples of solvates include compounds of the invention in combination with solvents such, for example, water (to form the hydrate), isopropanol, ethanol, methanol, dimethyl sulfoxide, ethyl acetate, acetic acid, ethanolamine, or acetone. Also included are formulations of solvate mixtures such as a compound of the invention in combination with two or more solvents.

The term "body mass index" (BMI) is used to mean a statistical measurement which compares a person's weight and height. Though it does not actually measure the percentage of body fat, it is a useful tool to estimate a healthy body weight based on how tall a person is. Body mass index is defined as the individual's body weight divided by the square of their height. The formulas universally used in medicine produce a unit of measure of $kg/m^2$.

As used herein, the term "UI" or "IU" refers to a unit of measurement for the amount of a substance; the mass or volume that constitutes one international unit varies based on which substance is being measured, and the variance is based on the biological activity or effect, for the purpose of easier comparison across substances. International units are used to quantify vitamins, hormones, some medications, vaccines, blood products, and similar biologically active substances. Many biological agents exist in different forms or preparations (e.g. vitamin A in the form of retinol or beta-carotene). The goal of the IU is to be able to compare these, so that different forms or preparations with the same biological effect will contain the same number of IUs. To do so, the WHO Expert Committee on Biological Standardization provides a reference preparation of the agent, arbitrarily sets the number of IUs contained in that preparation, and specifies a biological procedure to compare other preparations of the same agent to the reference preparation. Since the number of IUs contained in a new substance is arbitrarily set, there is no equivalence between IU measurements of different biological agents. For instance, one IU of vitamin E cannot be equated with one IU of vitamin A in any way, including mass or efficacy. For example: vitamin A: 1 IU is the biological equivalent of 0.3 µg retinol, or of 0.6 µg beta-carotene; vitamin C: 1 IU is 50 µg L-ascorbic acid; vitamin D: 1 IU is the biological equivalent of 25 ng cholecalciferol/ergocalciferol; vitamin E: 1 IU is the biological equivalent of about 0.667 mg d-alpha-tocopherol (⅔ mg exactly), or of 0.45 mg of dl-alpha-tocopherol acetate.

As used herein, the letter "g", when used alone, refers to grams, the term "mg" refers to milligrams, the term "µm" refers to micrograms, and the term "ml" refers to millilitres.

As used herein, the expression "dosage unit" or "dose unit" or "unit dose" refers to an amount of a substance (or combination of substances) administered to an individual in a single dose.

The term "obesity" is used to mean a condition in which excess body fat has accumulated to such an extent that health may be negatively affected. It is commonly defined as a BMI of about 30 $kg/m^2$ or higher. This distinguishes it from being "overweight," as defined by a BMI of between about 25 $kg/m^2$ and 29.9 $kg/m^2$.

As used herein, the expression "bariatric individual" refers to an individual with a Body Mass Index (BMI) exceeding a healthy range and which is candidate for bariatric surgery or who has undergone bariatric surgery.

As used herein, the expression "post-bariatric surgery patient" refers to a person who has undergone bariatric surgery. As used herein, the expression "bariatric surgery" includes a variety of procedures performed on a person who suffers from obesity. Procedures can be grouped in three main categories: malabsorptive, restricting, and mixed. Malabsorptive procedures attempt to block absorption of food and reduce the size of the stomach. Malabsorptive procedures include: biliopancreatic diversion, jejunoileal bypass and endoluminal sleeve. Restrictive procedures attempt to shrink the size of the stomach or take up space inside the stomach, making people feel satiety when they eat less. Restrictive procedures include: vertical banded gastroplasty, adjustable gastric band, sleeve gastrectomy, intragastric balloon and stomach folding. Mixed procedures combine restrictive and malabsorptive effects at the same time. Mixed procedures include: gastric bypass surgery, sleeve gastrectomy with duodenal switch and implantable gastric stimulation.

The present technology attempts at ameliorating and/or preventing disorders and/or conditions that may arise in bariatric individuals as well as in post-bariatric surgery patients. Examples of such disorders and/or conditions include, but are not limited to, nutritional deficiencies, inability to have sufficient food intake, inability to have sufficient protein intake, inability to have sufficient micronutrient intake, symptoms coming from high product osmolarity, symptoms caused by high glucose and insulin peaks, coronary heart disease, unhealthy gut, loss of nitrogen, loss of muscle mass, calcium deficiency, osteopenia, iron deficiency, inflammation or the like. The present technology may thus be used to treat the above-described disorders and/or conditions in obese pre- and post-bariatric surgery patients.

In some embodiments, the present technology attempts at ameliorating and/or preventing metabolic derangements that are the result of nutritional deficiencies. The metabolic derangements prevented could lead to sub-clinical states where there are no apparent symptoms but where metabolic functions are deranged. In other instances, the metabolic changes could lead to symptoms that are clinically significant.

In some instances, the present technology attempts at ameliorating and/or preventing vitamins deficiencies in bariatric individuals as well as in post-bariatric surgery patients.

In some instances, the present technology attempts at ameliorating and/or preventing mineral deficiencies in bariatric individuals as well as in post-bariatric surgery patients.

Deficiencies in vitamins and/or minerals can affect numerous metabolic functions such as the conversion of carbohydrates to energy, normal muscle function (including the heart muscle), oxidative carboxylation reactions, mitochondrial respiratory chain, coenzyme FAD and FMN formation, oxidation-reduction reactions in all cells, enzymatic reactions (mainly in protein and amino acid metabolisms), metabolism of fats and carbohydrates, Krebs cycle, synthesis of carnitine, catecholamines, adrenaline and noradrenaline, synthesis of cortisol, antioxidant, metabolic pathways involving cell growth, replication, survival of cells in culture. These deficiencies can lead to numerous symptoms such as lack of energy, constipation, nausea, vomiting, depression, neuropathy, ataxia, confusion, Wernicke-Korsakoff Syndrome, decreased cardiovascular function, osteopenia, osteoporosis, skin problems, anemia, decreased learning capacity, insulin resistance, diarrhea, hypogonadism, neutropenia, bleeding, muscular cramping and arrhythmia.

According to one embodiment, the present technology provides a nutritional formulation for bariatric individuals. In some implementations of this embodiment, the bariatric individual is a post-bariatric surgery patient.

In some implementations of this embodiment, the nutritional formulation comprises a first dosage unit and a second dosage unit. The first dosage unit is a multi-nutrients dosage unit and the second dosage unit is a mineral dosage unit.

Both the multi-nutrients dosage unit and the minerals dosage unit will be described in greater details below.

i) Multi-Nutrients Dosage Unit

In some implementations, the multi-nutrients dosage unit comprises vitamins.

In some implementations, the multi-nutrients dosage unit comprises vitamins and minerals.

In some implementations, the multi-nutrients dosage unit comprises a combination of vitamins and minerals.

Examples of vitamins that may be included in the multi-nutrients dosage unit include, but are not limited to: vitamin A (retinol, retinal, carotenoids (e.g., beta carotenes)), vitamin B, vitamin $B_1$ (thiamine), vitamin $B_2$ (riboflavin), vitamin $B_3$ (niacin, niacinamide, nicotinamide riboside), vitamin $B_5$ (pantothenic acid), vitamin $B_6$ (pyridoxine, pyridoxamine, pyridoxal), vitamin $B_7$ (biotin), vitamin $B_9$ (folates), vitamin $B_{12}$ (cyanocobalamin, hydroxocobalamin, methylcobalamin, adenosylcobalamin), vitamin C (ascorbic acid), vitamin D (cholecalciferol, ergocalciferol), vitamin $D_1$ (ergocalciferol, lumisterol), vitamin $D_2$ (ergocalciferol), vitamin $D_3$ (cholecalciferol), vitamin $D_4$ (22-dihydroergocalciferol), vitamin $D_5$ (sitocalciferol), vitamin E (tocopherols, tocotrienols) and vitamin K (phylloquinone, menaquinones), as well as derivatives or precursors thereof.

In some implementations, the multi-nutrients dosage unit comprises one or more of: vitamin A, vitamin B, vitamin C, vitamin D, vitamin E and vitamin K, as well as derivatives or precursors thereof.

In some implementations, the multi-nutrients dosage unit comprises one or more of: vitamin A, vitamin B, vitamin $B_1$, vitamin $B_2$, vitamin $B_3$, vitamin $B_5$, vitamin $B_6$, vitamin $B_7$, vitamin $B_{12}$, vitamin C, vitamin $D_3$, vitamin E and vitamin K, as well as derivatives or precursors thereof.

Examples of minerals that may be included in the multi-nutrients dosage unit of the present disclosure include but are not limited to: calcium, copper, chloride, chromium, fluoride, iodine, iron, magnesium, phosphorus, potassium, sodium, selenium, manganese, molybdenum, nickel and zinc, in their native form or in their oxide, hydroxide, sulfides, sulfate, carbonate, phosphate or halide forms.

In some implementations, the multi-nutrients dosage unit comprises an alkaline mineral. As used herein, the expression "alkaline minerals" refers to minerals that have a pH higher than 7. Examples of alkaline earth mineral include magnesium, calcium, potassium, sodium, and lithium, in their native form or in their oxide, hydroxide, sulfides, sulfate, carbonate, phosphate or halide form.

In some implementations, the multi-nutrients dosage unit comprises calcium, in its native form or in its oxide, hydroxide, sulfides, glycinate, sulfate, lactate, carbonate, phosphate or halide form.

In some implementations, the multi-nutrients dosage unit comprises one or more of calcium, calcium citrate, calcium carbonate, calcium gluconate, calcium lactate, calcium phosphate, and calcium citrate malate, as well as derivatives or precursors thereof.

In some embodiments, the multi-nutrients dosage unit comprises between about 1 mg and about 10 g of vitamins. In some implementations, the multi-nutrients dosage unit comprises between about 1 mg and about 5 g, or between about 10 mg and about 10 g, or between about 10 mg and about 5 g or between about 5 mg and about 5 g of vitamins.

In the instances where the multi-nutrients dosage unit comprises vitamin A, the amount of vitamin A in the dosage is between about 65 µg and about 3050 µg, or is between about 215 IU and about 10000 IU, or is between about 500 µg and about 1 mg. In the instances where the multi-nutrients dosage unit comprises vitamin $B_1$, the amount of vitamin $B_1$ in the dosage is between about 0.05 mg and about 100 mg. In the instances where the multi-nutrients dosage unit comprises vitamin $B_2$, the amount of vitamin $B_2$ in the dosage is between about 0.05 mg and about 100 mg, or between about 0.1 mg and about 10 mg, or between about 1 mg and about 2 mg. In the instances where the multi-nutrients dosage unit comprises vitamin $B_3$, the amount of vitamin $B_3$ in the dosage is between about 1 mg and about 100 mg, or between about 10 mg and about 25 mg. In the instances where the multi-nutrients dosage unit comprises vitamin $B_5$, the amount of vitamin $B_5$ in the dosage is between about 0.4 mg and about 100 mg, or between about 1 mg and about 50 mg, or between about 1 mg and about 10 mg. In the instances where the multi-nutrients dosage unit comprises vitamin $B_6$, the amount of vitamin $B_6$ in the dosage is between about 0.1 mg and about 100 mg, or between about 1 mg and about 50 mg, or between about 1 mg and about 2 mg. In the instances where the multi-nutrients dosage unit comprises vitamin $B_7$, the amount of vitamin $B_7$ in the dosage is between about 1.5 µg and about 100 µg, or between about 25 µg and about 50 µg. In the instances where the multi-nutrients dosage unit comprises vitamin $B_9$, the amount of vitamin $B_9$ in the dosage is between about 30 µg and about 1000 µg, or between about 200 µg and about 500 µg. In the instances where the multi-nutrients dosage unit comprises vitamin $B_{12}$, the amount of vitamin $B_{12}$ in the dosage is between about 0.1 µg and about 2500 µg, or between about 10 µg and about 500 µg, or between about 200 µg and about 500 µg. In the instances where the multi-nutrients dosage unit comprises vitamin C, the amount of vitamin C in the dosage is between about 5 mg and about 2000 mg, or between about 50 mg and 1000 mg, or between about 50 mg and about 500 mg, or between about 50 mg and about 100 mg. In the instances where the multi-nutrients dosage unit comprises vitamin D, the amount of vitamin D in the dosage is between about 10 µg and about 100 µg or is between about 400 IU and about 4000 IU; or between about 20 µg and about 100 µg, or between about 25 µg and 50 µg. In the instances where the multi-nutrients dosage unit comprises vitamin D3, the amount of vitamin $D_3$ in the dosage is between about 1 µg and about 65 µg or is between about 40 IU and about 2500 IU, or between about 20 µg and about 100 µg, or between about 25 µg and 50 µg. In the instances where the multi-nutrients dosage unit comprises vitamin E, the amount of vitamin E in the dosage is between about 1 mg and about 1000 mg or is between about 1 IU and about 1500 IU, or between about 10 mg and about 100 mg. In the instances where the multi-nutrients dosage unit comprises vitamin K, the amount of vitamin K in the dosage is between about 6 µm and about 200 µm, or between about 50 µm and about 250 µm.

In some embodiments, the multi-nutrients dosage unit comprises between about 1 mg and about 5 g of minerals. In some implementations, the multi-nutrients dosage unit comprises between about 10 mg and about 5 g, between about 1 mg and about 2 g, between about 10 mg and about 2 g, or between about 10 mg and about 1 g of minerals.

In the instances where the multi-nutrients dosage unit comprises copper, the amount of copper in the dosage is between about 0.05 mg to about 10 mg, or between about 0.5 mg and about 5 mg. In the instances where the multi-nutrients dosage unit comprises chloride, the amount of chloride in the dosage is between about 0.15 g and about 2.5 g. In the instances where the multi-nutrients dosage unit comprises chromium, the amount of chromium in the dosage is between about 2 µm and about 500 µm, or between about 10 µm and about 50 µm. In the instances where the multi-nutrients dosage unit comprises fluoride, the amount of fluoride in the dosage is between about 0.01 mg and about 4 mg. In the instances where the multi-nutrients dosage unit comprises iodine, the amount of iodine in the dosage is between about 0.01 mg to about 1 mg, or between about 0.1 mg and about 0.25 mg. In the instances where the multi-nutrients dosage unit comprises iron, the amount of iron in the dosage is between about 1 mg and about 150 mg, or between about 10 mg and about 100 mg. In the instances where the multi-nutrients dosage unit comprises magnesium, the amount of magnesium in the dosage is between about 20 mg and about 500 mg, or between about 25 mg and 100 mg. In the instances where the multi-nutrients dosage unit comprises phosphorus, the amount of phosphorus in the dosage is between about 100 mg and about 1250 mg. In the instances where the multi-nutrients dosage unit comprises potassium, the amount of potassium in the dosage is between about 0 mg and about 200 mg, or between about 20 mg and about 50 mg. In the instances where the multi-nutrients dosage unit comprises sodium, the amount of sodium in the dosage is between about 0.1 g and about 1.5 g. In the instances where the multi-nutrients dosage unit comprises selenium, the amount of selenium in the dosage is between about 3.0 µm to about 200 µm, or between about 25 µm and 100 µm. In the instances where the multi-nutrients dosage unit comprises manganese, the amount of manganese in the dosage is between about 0.1 mg and about 10 mg, or between about 1 mg and about 5 mg. In the instances where the multi-nutrients dosage unit comprises molybdenum, the amount of molybdenum in the dosage is between about 2 µm and about 2000 µm, or between about 10 µm and about 100 µm. In the instances where the multi-nutrients dosage unit comprises zinc, the amount of zinc in the dosage is between 0.5 mg and about 50 mg, or between about 5 mg and about 25 mg. In the instances where the multi-nutrients dosage unit comprises calcium, the amount of calcium in the dosage is between about 50 mg and about 2000 mg.

In some implementations, the multi-nutrients dosage unit comprises nickel.

In some implementations, the multi-nutrients dosage unit comprises cobalt.

In some implementations, the multi-nutrients dosage unit comprises lutein.

In some implementations, the multi-nutrients dosage unit comprises lycopene.

The multi-nutrients dosage unit of the present technology may also comprise inactive components such as for example carriers, excipients, fillers or binders, disintegrating agents, lubricating agents, silica flow conditioners and stabilizing agents or the like, which may impart suitable or desirable characteristics to the dosage form such as taste, texture, viscosity, or the like. Disintegrating agents may assist in the dissolution of the tablet. Disintegrating agents are well known in the art and include, but are not limited to alginic acid, carboxymethylcellulose, carboxymethylcellulose sodium, hydroxypropylcellulose (low substituted), microcrystalline cellulose, powdered cellulose, colloidal silicon dioxide, sodium croscarmellose, crospovidone, methylcellulose, polacrilin potassium, povidone, sodium alginate, sodium starch glycolate, starch, disodium di sulfite, disodium edathamil, disodium edetate, disodiumethylenediaminetetraacetate (EDTA), crosslinked polyvinylpyrollidines, pregelatanized starch, carboxymethyl starch, sodium carboxymethylstarch, microcrystalline cellulose. Lubricating agents assist in the compression of the formulation. Lubricating agents are well known in the art and include, but are not limited to calcium stearate, canola oil, glyceryl palmitosstearate, hydrogenated vegetable oil (type I), magnesium oxide, magnesium stearate, mineral oil, poloxamer, polyethylene glycols, sodium lauryl sulfate, sodium stearate fumarate, stearic acid, talc, zinc stearate, glyceryl behapate, magnesium lauryl sulfate, boric acid, sodium benzoate, sodium acetate, sodium benzoatelsodium acetate (in combination) and D,L-leucine. Fillers or binders include, but are not limited to acacia, alginic acid, calcium phosphate (dibasic), carboxymethylcellulose, carboxymethylcellulose sodium, hydroxy ethylcellulose, hydroxypropylcellulose, hydroxypropylmethylcellulose, dextrin, dextrates, sucrose, tylose, pregelatinized starch, calcium sulfate, amylose, glycine, bentonite, maltose, sorbitol, ethylcellulose, disodium hydrogen phosphate, disodium phosphate, disodium pyrosulfite, polyvinyl alcohol, gelatin, glucose, guar gum, liquid glucose, compressible sugar, magnesium aluminum silicate, maltodextrin, polyethylene oxide, polymethacrylates, povidone, sodium alginate, microcrystalline cellulose, starch and zein. Many other pharmaceutically acceptable tableting agents such as fillers or binders, lubricating agents, disintegrating agents, silica flow conditioners and stabilizing agents known in the pharmaceutical arts may be used in the multi-nutrients dosage units of the present technology (see, e.q. Remington: The Science and Practice of Pharmacy, 20th Edition, 2000, Lippincott Williams & Wilkins; Kibbe: Handbook of Pharmaceutical Excipients, 3rd Edition, 2000, American Pharmaceutical Association), incorporated herein by reference. As used herein, the expression "pharmaceutically acceptable" is any agent suitable for use in humans without undue side effects, such as irritation, toxicity, or allergic response.

In one embodiment, the multi-nutrients dosage unit is in a form suitable for oral administration. In some implementations of this embodiment, the multi-nutrients dosage unit is in a solid form. For instances, the multi-nutrients dosage unit may be a tablet, a pill, a capsule, a caplet, or a flowable powder. Solid multi-nutrients dosage units may vary in shape and may be, for example, round, ovoid, oblong, cylindrical (e.g., disk-shaped) or any other geometric shape, for example rectilinear. For example, the dosage form can have a disk or ovoid shape, or a shape like a flattened disk or torpedo. The edges can be beveled or rounded.

When desired, the multi-nutrients dosage unit of the present technology can be formulated with enteric coatings adapted for sustained or controlled release administration of the dosage form.

The multi-nutrients dosage unit of the present technology may be prepared by any of the methods well known in the art. Techniques and formulations generally are found in for example, Remington's Pharmaceutical Sciences (Mack Publishing Co., Easton, Pa.). Such methods include the step of bringing into an association of one or more ingredients with any inactive components. In general, the dosage forms are prepared by uniformly and intimately bringing into association the ingredients with liquid carriers or finely divided solid carriers or both, and then, if necessary, shaping the product or filling capsules. Methods of preparation of tablets are well known to one of ordinary skill in the art. See, e.g., Pharmaceutical Dosage Forms: Tablets, Third Edition, by Larry L. Augsburger and Stephen W. Hoag (publisher: Informa Healthcare; Dec. 15, 2007). These methods include direct compression and granulation (e.g., wet or dry or fluid-bed). The pellets can be made by, for example, simple granulation such as wet granulation or dry granulation, followed by sieving; extrusion and marumerization (spheronization); rotogranulation; or any agglomeration process that results in a pellet of reasonable size and robustness. For extrusion and marumerization, the ingredients are granulated by addition of a binder solution. The wet mass is passed through an extruder equipped with a certain size screen, and the extrudates are spheronized in a marumerizer. The resulting pellets are dried and sieved for further applications. One may also use high-shear granulation, wherein ingredients are dry-mixed and then the mixture is wetted by addition of a binder solution in a high shear-granulator/mixer. The granules are kneaded after wetting by the combined actions of mixing and milling. The resulting granules or pellets are dried and sieved for further applications. Alternatively, the immediate release beads or pellets are prepared by solution or suspension layering, whereby a solution or dispersion of the ingredients, with or without a binder and optionally an anti-tacking agent such as talc, is sprayed onto a core or starting seed (either prepared or a commercially available product) in a fluid bed processor or other suitable equipment. The cores or starting seeds can be, for example, sugar spheres or spheres made from microcrystalline cellulose. The ingredients, thus, are coated on the surface of the starting seeds. The ingredients may also be layered onto the ingredients-containing pellets described above, if desired. Following drug layering, the resulting ingredients-loaded pellets are dried for further applications. A protective layer, or overcoating, may be desired to ensure that the ingredients-loaded pellets do not aggregate during processing or upon storage. The protective coating layer may be applied immediately outside the core, either an ingredients-containing core or an ingredients-layered core, by conventional coating techniques such as pan coating or fluid bed coating using solutions of polymers in water or suitable organic solvents or by using aqueous polymer dispersions. OPADRY®, OPADRY II® (Colorcon) and corresponding color and colorless grades from Colorcon can be used to protect the pellets from being tacky and provide colors to the product. Different anhydride-based polymers (e.g., sebacic/fumaric copolymers such as Spheromer™ I or Spheromer™ II from Spherics, Inc.) may also be used as protective layer. In certain embodiments, many ingredients can be incorporated into the overcoating formula, for example to provide a quicker immediate release, such as plasticizers: acetyltriethyl citrate, triethyl citrate, acetyltributyl citrate; dibutylsebacate, triacetin, polyethylene glycols, propylene glycol and the others; lubricants: talc, colloidal silica dioxide, magnesium stearate, calcium stearate, titanium dioxide, magnesium silicate, and the like.

In yet other implementation, the multi-nutrients dosage unit is in capsule form. Diverse capsule manufacturing and design methods are well known to one of ordinary skill in the art. See, e.g., Pharmaceutical Preformulation and Formulation: A Practical Guide from Candidate Drug Selection to Commercial Dosage Form, by Mark Gibson (publishers: Informa Healthcare, Aug. 1, 2001). When the dose form is a capsule, the method further comprises preparing the formulations into a form for loading and/or delivery, e.g., as a tablet, capsule and/or powder, and loading the formulations into the capsule to form the unit dose.

ii) Minerals Dosage Unit

In some implementations, the minerals dosage unit of the present technology comprises an alkaline mineral. As used hereon, the expression "alkaline mineral" refers to a mineral that has a pH higher than 7. Examples of an alkaline mineral include magnesium, calcium, potassium, sodium, and lithium, in their native form or in their oxide, hydroxide, sulfides, sulfate, carbonate, phosphate or halide form.

In some implementations, the minerals dosage unit comprises calcium. In some instances, calcium is present in the minerals dosage unit in its native form or in its oxide, hydroxide, sulfides, sulfate, carbonate, phosphate or halide form.

In some implementations, the minerals dosage unit comprises one or more of calcium, calcium citrate, calcium carbonate, calcium gluconate, calcium lactate, calcium phosphate, and calcium citrate malate, as well as derivatives thereof.

In some embodiments, the minerals dosage unit comprises between about 50 mg and about 2000 mg of alkaline mineral. In some implementations, the multi-nutrients dosage unit comprises between about 100 mg and about 1000 mg of alkaline mineral.

In one embodiment, the minerals dosage unit is suitable for oral administrations. In some of this embodiment, the minerals dosage unit is in liquid form. In some instances, the liquid form is suitable for oral administration. Liquid forms suitable for oral administration include liquid form preparations including emulsions, syrups, elixirs, aqueous solutions, aqueous suspensions, or solid form preparations which are intended to be converted shortly before use to liquid form preparations. Emulsions can be prepared in solutions, for example, in aqueous propylene glycol solutions or may contain emulsifying agents, for example, such as lecithin, sorbitan monooleate, or acacia. Aqueous solutions can be prepared by dissolving the alkaline mineral of the present technology in water and adding suitable colorants, flavors, stabilizers, and thickening agents. Aqueous suspensions can be prepared by dispersing the finely divided components in water with viscous material, such as natural or synthetic gums, resins, methylcellulose, sodium carboxymethylcellulose, and other well known suspending agents. Solid form preparations include solutions, suspensions, and emulsions, and can comprise, in addition to the alkaline minerals of the present technology, colorants, flavors, stabilizers, buffers, artificial and natural sweeteners, dispersants, thickeners, solubilizing agents, and the like.

In some implementations of this embodiment, the liquid form is suitable to be drunk and thus has a viscosity below 150 mPas, preferably below 100 mPas, more preferably below 80 mPas, even more preferably below 70 mPas. The viscosity is determined in a rotational rheometer using a cone-plate geometry at 20° C. at a shear rate of 50 1/s. In other implementations, the liquid form is a texturized product ready for consumption to be eaten with a spoon and thus having a viscosity of at least 350 mPas, preferably above 750 mPas, more preferably between 1000 and 4000 mPas.

Since post-bariatric surgery patients have a small stomach volume, the volume of the liquid form is to be kept low. Preferably the volume of a single dose should not exceed 150 ml per dose, more preferably no more than 125 ml and even more preferably less than 100 ml. In some instances, the volume of a single dose is between about 5 ml and 25 ml.

In some instances, the multi-nutrients dosage unit is in solid form. In some instances, the minerals dosage unit is in liquid form. In some other instances, the multi-nutrients dosage unit and the minerals dosage unit are both in solid form. In some other instances, the multi-nutrients dosage unit and the minerals dosage unit are both in liquid form. In some other instances, the multi-nutrients dosage unit is in liquid form and the minerals dosage unit is in solid form.

iii) Nutritional Formulation Regimen

In certain embodiments, the nutritional formulation of the present technology is administered once daily (i.e., one time per day) and the nutritional formulation comprises the multi-nutrients dosage unit and the mineral dosage unit. In some implementations, the multi-nutrients dosage unit and the minerals dosage unit are administered simultaneously. In some other implementations, the multi-nutrients dosage unit and the mineral dosage unit are administered one after the other. In some implementations, the multi-nutrients dosage unit is administered first and the minerals dosage unit is administered second. In other implementations, the minerals dosage unit is administered first and the multi-nutrients dosage unit is administered second.

In the embodiments wherein the nutritional formulation of the present technology is administered once daily, the daily dose of the multi-nutrients is between about 2 mg and about 15 g.

In the embodiments wherein the nutritional formulation of the present technology is administered once daily, the daily dose of the minerals is between about 50 mg and about 2 g.

In certain embodiments, the nutritional formulation of the present technology is administered twice daily (i.e., two times per day) and the nutritional formulation comprises the multi-nutrients dosage unit and the mineral dosage unit. In such embodiments, the total daily dose of the multi-nutrients is between about 4 mg and about 30 mg and the total daily dose of the minerals is between about 100 mg and about 4 g.

In certain embodiments, the nutritional formulation of the present technology is administered three times daily (i.e., three times per day) and the nutritional formulation comprises the multi-nutrients dosage unit and the mineral dosage unit. In such embodiments, the total daily dose of the multi-nutrients is between about 6 mg and about 45 g and the total daily dose of the minerals is between about 150 mg and about 6 g.

In certain embodiments, the multi-nutrients dosage unit of the nutritional formulation is administered twice daily while the mineral dosage unit is administered once daily. In other embodiments, the multi-nutrients dosage unit of the nutritional formulation is administered once daily while the mineral dosage unit is administered every two days.

In the embodiments, wherein the nutritional formulation is administered more than once daily, the time between administrations is at least 3 hours, at least 4 hours, at least 5 hours, at least 6 hours, at least 7 hours or at least 8 hours. For example, in the embodiment wherein the nutritional formulation is administered twice daily, the first dose may be administered in the morning whereas the second dose is administered in the evening.

In some embodiments, the minerals dosage unit is administered in the mornings and in the evening whereas the multi-nutrients dosage unit is administered at mid-day (e.g., lunch time).

In some embodiments, one dose unit of the nutritional formulation of the present technology comprises between about 10 mg and about 5 g of vitamins, between about 10 mg and about 1 g of minerals and between about 100 mg and about 1 g of alkaline mineral.

In some embodiments, two dose units of the nutritional formulation of the present technology comprises between about 1 mg and about 10 g of vitamins, between about 1 mg and about 1 g of minerals and between about 100 mg and about 1 g of alkaline mineral.

In some embodiments, two dose units of the nutritional formulation of the present technology comprises between about 100 mg and about 500 mg of vitamins, about 50 mg and about 500 mg of minerals and between about 100 mg and about 1 g of alkaline mineral.

In some of these embodiments, the alkaline mineral is in a liquid form and the liquid is between about 5 ml and about 50 ml, or between about 10 ml and about 25 ml, or between about 10 ml and about 20 ml, or about 15 ml.

In some embodiments, the nutritional formulation of the present technology is administered once daily for a period of at least one month, at least two months, at least 3 months, at least four months, at least five months, at least six months, at least seven months, at least eight months, at least nine months, at least 10 months, at least eleven months, at least 12 months, at least two years, at least five years or at least ten years. In some embodiments, the nutritional formulation of the present technology is administered until the bariatric individual demonstrates a stable weight or stable BMI.

The initial administration of the nutritional formulation of the present technology may occur on the same day of or the day after bariatric surgery. In some instances, the initial administration of the nutritional formulation of the present technology occurs upon the patient being discharged from the hospital. In some other instances, the initial administration of the nutritional formulation of the present technology occurs before bariatric surgery and is pursued after bariatric surgery.

iv) Nutritional Formulation Kit

According to another embodiment, the present technology provides a nutritional kit for bariatric individuals. In some implementations of this embodiment, the nutritional kit of the present technology comprises a plurality of types of dosage units along with instructions for taking the dosage units, the plurality of dosage units comprising the multi-nutrients dosage unit and the minerals dosage unit.

In one embodiment, the present technology provides a nutritional kit for bariatric individuals comprising two distinct types of dosage units, wherein a first type of dosage unit comprises the multi-nutrients dosage unit and wherein a second type of dosage unit comprises the minerals dosage unit.

In one embodiment, the present technology provides a nutritional kit for bariatric individuals comprising the following components: (1) from about 7 days to about a month-supply of dosage units of a first type, each dosage unit of the first type comprising the multi-nutrients dosage unit, and (2) from about 7 days to about a month-supply of dosage units of a second type, each dosage unit of the second type comprising the minerals dosage unit. In some implementations of this embodiment, the nutritional kit further comprises a means for having the components arranged in a way as to facilitate compliance with the regimen, the means including instructions for daily intake of a dosage unit of the first type and indications for daily intake of a dosage unit of the second type to be either (a) taken daily at a predetermined time interval; or (b) cycled by periodical discontinuation when and if side-effects are encountered.

In some implementations of these embodiments, the nutritional kit for bariatric individuals of the present technology may comprise between about 10 mg (7 days) and about 450 mg (30 days) of multi-nutrients dosage unit.

In some implementations of these embodiments, the nutritional kit for bariatric individuals of the present technology may comprise between about 350 mg (7 days) and about 60 g (30 days) of multi-nutrients dosage unit.

In some implementations of these embodiments, the nutritional kit for bariatric individuals of the present technology may comprise between about 700 mg (7 days) and about 30 g (30 days) of minerals dosage form. In some of these implementations, the minerals dosage form is in liquid form. The amount of liquid is between about 35 ml (7 days) and about 750 ml (30 days).

In some embodiments, the nutritional kit for bariatric individuals of the present technology includes a first container comprising a first dosage unit that includes the multi-nutrients dosage unit, and a second container comprising a second dosage unit that includes the minerals dosage form.

In some embodiments, the nutritional kit for bariatric individuals of the present technology includes one or more containers of a first type each comprising a portion of the dosage unit of the multi-nutrients dosage unit, and a container of a second type comprising a second dosage unit that includes the minerals dosage form.

The containers may be light impermeable, air-tight and/or leak resistant. Exemplary containers include, but are not limited to, vials, bottles, or pouches.

Written instructions on how to use the nutritional formulation in accordance with the present disclosure may be included in the kit, or may be included on or associated with the containers comprising the dose unit of the present disclosure.

Identification of equivalent compositions, methods and kits are well within the skill of the ordinary practitioner and would require no more than routine experimentation, in light of the teachings of the present disclosure. Practice of the disclosure will be still more fully understood from the following examples, which are presented herein for illustration only and should not be construed as limiting the disclosure in any way.

EXAMPLE

The example below is given to illustrate the practice of various embodiments of the present disclosure. It is not intended to limit or define the entire scope of this disclosure. It should be appreciated that the disclosure is not limited to the particular embodiments described and illustrated herein but includes all modifications and variations falling within the scope of the disclosure as defined in the appended embodiments.

Example 1—Preparation of a Nutritional Formulation

A nutritional formulation was prepared with the components identified in Table 2.

TABLE 2

| Components of the nutritional formulation Nutritional formulation | | |
|---|---|---|
| | Component | Amount per dose |
| Multi-nutrients dosage unit (solid form) | Vitamin A | 2500 UI or 750 µg |
| | Vitamin B1 | 25 mg |
| | Vitamin B2 | 1.3 mg |
| | Vitamin B3 | 16 mg |
| | Vitamin B5 | 5 mg |
| | Vitamin B6 | 1.3 mg |
| | Biotin | 0.03 mg |
| | Folic acid | 0.4 mg |
| | Vitamin B12 | 250 µg |
| | Vitamin C | 90 mg |
| | Vitamin D3 | 1000 UI or 25 µg |
| | Vitamin E | 50 UI or 33.6 µg |
| | Vitamin K | 120 µg |
| | Chromium | 35 µg |
| | Copper | 1 mg |

TABLE 2-continued

| Components of the nutritional formulation Nutritional formulation | | |
|---|---|---|
| | Component | Amount per dose |
| | Iodine | 0.15 mg |
| | Iron | 30 mg |
| | Magnesium | 50 mg |
| | Manganese | 2.3 mg |
| | Molybdenum | 0.045 mg |
| | Selenium | 55 µg |
| | Zinc | 11 mg |
| | Potassium | 40 mg |
| | Filler | 800-1000 mg |
| Minerals dosage unit (liquid form) | Calcium citrate | 500 mg/15 ml |

The components of the multi-nutrients dosage unit were mixed together and compounded to obtain a tablet having a weight of between about 750 mg and 1100 mg.

The invention claimed is:

1. A nutritional formulation for administration to bariatric individuals; comprising:
   a) a multi-nutrient dosage unit comprising: i) a total amount of minerals ranging between about 50 mg and about 500 mg; and ii) a total amount of vitamins ranging between about 100 mg and about 500 mg; wherein the total amount of minerals includes between about 10 mg and about 100 mg of iron, between about 0.1 mg and about 0.25 mg of iodine and between about 25 mg and about 100 mg of magnesium; and
   b) an alkaline mineral unit comprising calcium, wherein the alkaline mineral unit is present in the nutritional formulation in an amount ranging from between about 100 mg and about 1 g.

2. The nutritional formulation according to claim 1, wherein the nutritional formulation is suitable for oral administration.

3. The nutritional formulation according to claim 1, wherein the multi-nutrients dosage unit is in a solid form.

4. The nutritional formulation according to claim 1, wherein the minerals dosage unit is in a liquid form.

5. The nutritional formulation according to claim 1, wherein the vitamin is selected from vitamin A, vitamin $B_1$, vitamin $B_2$, vitamin $B_3$, vitamin $B_5$, vitamin $B_6$, vitamin $B_7$, vitamin $B_9$, vitamin $B_{12}$, vitamin C, vitamin $D_1$, vitamin $D_2$, vitamin $D_3$, vitamin $D_4$, vitamin $D_5$, vitamin E and vitamin K, derivatives and precursors thereof.

6. The nutritional formulation according to claim 1, wherein the vitamin is selected from vitamin A, vitamin B, vitamin C, vitamin D, vitamin E and vitamin K, as well as derivatives or precursors thereof.

7. The nutritional formulation according to claim 1, wherein the vitamin is selected from vitamin A, vitamin $B_1$, vitamin $B_2$, vitamin $B_3$, vitamin $B_5$, vitamin $B_6$, vitamin $B_7$, vitamin $B_{12}$, vitamin C, vitamin $D_3$, vitamin E and vitamin K, as well as derivatives or precursors thereof.

8. The nutritional formulation according to claim 1, wherein the mineral further comprises copper, chloride, chromium, fluoride, phosphorus, potassium, sodium, selenium, manganese, molybdenum, nickel and zinc.

9. The nutritional formulation according to claim 8, wherein the mineral is in a oxide, hydroxide, sulfides, sulfate, carbonate, phosphate or halide form.

10. The nutritional formulation according to claim 1, wherein the calcium is in an oxide, hydroxide, sulfide, sulfate, carbonate, phosphate or halide form.

11. The nutritional formulation according to claim 1, wherein the calcium is calcium citrate, calcium carbonate, calcium gluconate, calcium lactate, calcium phosphate, or calcium citrate malate, or a derivative thereof.

12. The nutritional formulation according to claim 1, wherein the multi-nutrients dosage unit comprises vitamin A in an amount of between about 215 IU and about 10000 IU.

13. The nutritional formulation according to claim 1, wherein the multi-nutrient dosage unit comprises vitamin $B_1$ in an amount of between about 0.05 mg and about 100 mg.

14. The nutritional formulation according to claim 1, wherein the multi-nutrient dosage unit comprises vitamin $B_2$ in an amount of between about 0.05 mg and about 100 mg.

* * * * *